(12) United States Patent
Dinsmore

(10) Patent No.: US 6,920,202 B1
(45) Date of Patent: Jul. 19, 2005

(54) THERAPEUTIC RADIATION SOURCE WITH IN SITU RADIATION DETECTING SYSTEM

(75) Inventor: Mark Dinsmore, Sudbury, MA (US)

(73) Assignee: Carl-Zeiss-Stiftung, Oberkochen (DE)

( * ) Notice: Subject to any disclaimer, the term of this patent is extended or adjusted under 35 U.S.C. 154(b) by 372 days.

(21) Appl. No.: 10/005,290

(22) Filed: Dec. 4, 2001

(51) Int. Cl.[7] .............................................. G21G 4/00
(52) U.S. Cl. ........................ 378/119; 378/121; 378/65
(58) Field of Search ................................ 378/119, 121, 378/65, 62, 165; 600/1

(56) References Cited

U.S. PATENT DOCUMENTS

| | | | |
|---|---|---|---|
| 5,090,043 A | | 2/1992 | Parker et al. |
| 5,153,900 A | | 10/1992 | Nomikos et al. |
| RE34,421 E | | 10/1993 | Parker et al. |
| 5,369,679 A | | 11/1994 | Sliski et al. |
| 5,422,926 A | | 6/1995 | Smith et al. |
| 5,428,658 A | * | 6/1995 | Oettinger et al. ............ 378/119 |
| 5,606,163 A | * | 2/1997 | Huston et al. .............. 250/337 |
| 5,621,780 A | | 4/1997 | Smith et al. |
| 6,319,188 B1 | * | 11/2001 | Lovoi ............................ 600/3 |
| 6,320,935 B1 | * | 11/2001 | Shinar et al. ............... 378/199 |
| 6,324,257 B1 | | 11/2001 | Halavee |

FOREIGN PATENT DOCUMENTS

| | | |
|---|---|---|
| WO | WO 93/04735 | 3/1993 |
| WO | WO 01/47596 | 7/2001 |

* cited by examiner

*Primary Examiner*—Craig E. Church
*Assistant Examiner*—Irakli Kiknadze
(74) *Attorney, Agent, or Firm*—McDermott, Will & Emery LLP

(57) ABSTRACT

A therapeutic radiation source includes an in situ radiation detecting system for monitoring in real time an amount of the therapeutic radiation that has been generated. An electron source generates electrons in response to light that is transmitted through a fiber optic cable and impinges upon the electron source. The electrons are accelerated toward the target and strike the target, causing the target to emit therapeutic radiation, such as x-rays. A scintillator is disposed along a path of a portion of the emitted therapeutic radiation, and generates scintillator light corresponding to the intensity of the therapeutic radiation that is incident upon the scintillator. A photodetector in optical communication with the scintillator produces a signal indicative of the intensity of the therapeutic radiation incident upon the scintillator.

35 Claims, 7 Drawing Sheets

THERAPEUTIC RADIATION SOURCE WITH IN SITU RADIATION DETECTING SYSTEM

CROSS-REFERENCE TO RELATED APPLICATIONS

Not Applicable

STATEMENT REGARDING FEDERALLY SPONSORED RESEARCH

Not Applicable

REFERENCE TO MICROFICHE APPENDIX

Not Applicable

FIELD OF THE INVENTION

The present invention relates to a miniaturized, low power radiation source for use in generating therapeutic radiation.

BACKGROUND

In the field of medicine, radiation may be used for diagnostic, therapeutic and palliative purposes. Therapeutic use of radiation such as x-rays and γ-rays typically involves-using these rays to eradicate malignant cells. Conventional radiation treatment systems used for medical treatment, such as the linear accelerators that produce high-energy x-rays, utilize a remote radiation source external to the targeted tissue. A beam of radiation is directed at the target area, for example a malignant tumor inside the body of a patient. The x-rays penetrate the patient's body tissue and deliver x-ray radiation to the cancer cells, usually seated deep inside the body. This type of treatment is referred to as teletherapy because the radiation source is located at some distance from the target. This treatment suffers from the disadvantage that tissue disposed between the radiation source and the target is exposed to radiation. To reach the cancer cells, the x-rays from an external radiation source must usually penetrate through normal surrounding tissues. Non-cancerous tissues and organs are thus also damaged by the penetrating x-ray radiation.

Brachytherapy, on the other hand, is a form of treatment in which the source of radiation is located close to, or in some cases within, the area receiving treatment. Brachytherapy, a word derived from the ancient Greek word for close ("brachy"), offers a significant advantage over teletherapy, because the radiation is applied primarily to treat only a predefined tissue volume, without significantly affecting the tissue adjacent to the treated volume. The term brachytherapy is commonly used to describe the use of "seeds," i.e. encapsulated radioactive isotopes, which can be placed directly within or adjacent the target tissue to be treated. Handling and disposal of such radioisotopes, however, may impose considerable hazards to both the handling personnel and the environment. Also, introduction of the radioisotopes requires invasive procedures which have potential side-effects, such as the possibility of infection. Moreover, there is no ability to provide selective control of time dosage or radiation intensity.

The term "x-ray brachytherapy" is defined for purposes of this application as x-ray radiation treatment in which the x-ray source is located close to or within the area receiving treatment. An x-ray brachytherapy system, which utilizes a miniaturized low power radiation source that can be inserted into, and activated from within, a patient's body is disclosed in U.S. Pat. No. 5,153,900 issued to Nomikos et al., U.S. Pat. No. 5,369,679 to Sliski et al., U.S. Pat. No. 5,422,926 to Smith et al., and U.S. Pat. No. 5,428,658 to Oettinger et al., all owned by the assignee-of the present application, all of which are hereby incorporated by reference. The x-ray brachytherapy systems disclosed in the above-referenced patents include miniaturized, insertable x-ray probes that are capable of controllably producing and delivering low power x-ray radiation, while positioned within or in proximity to a predetermined region to be irradiated. In this way, x-ray radiation need not pass through the patient's-skin, bone, or other tissue prior to reaching the target tissue. The probe may be fully or partially implanted into, or surface-mounted onto a desired area, within a treatment region of a patient. The insertable probe emits low power x-rays from a nominal, or effective "point" source located within or adjacent to the desired region to be irradiated, so that substantially only the desired region is irradiated, while irradiation of other regions are minimized. X-ray brachytherapy offers the advantages of brachytherapy, while avoiding the use and handling of radioisotopes. Also, x-ray brachytherapy allows the operator to control over time the dosage of the delivered x-ray radiation.

X-ray brachytherapy treatment generally involves positioning the insertable probe into or adjacent to the tumor, or into the site where the tumor or apportion of the tumor was removed, to treat the tissue adjacent the site with a local boost of radiation. X-ray probes of the type generally disclosed in U.S. Pat. No. 5,153,900 include a housing, and a hollow, tubular probe or catheter extending from the housing along an axis, and having an x-ray emitting target element at its distal end. The probe may enclose an electron source, such as a thermionic cathode. In one form of a thermionic cathode, a filament is resistively heated with a current. This in turn heats the cathode so that electrons are generated by thermionic emission.

In another form of an x-ray brachytherapy device, as disclosed in U.S. Pat. No. 5,428,658, an x-ray probe may include a flexible probe, such as a flexible fiber optical cable enclosed within a metallic sheath. The x-ray probe may also include a substantially rigid, evacuated capsule that is coupled to a distal end of the flexible probe. The capsule encloses an optically activated electron source, such as a photocathode, and an x-ray emissive target element. In a photocathode configuration, a photoemissive substance is irradiated by a LED or a laser source, causing the generation of free electrons. Typically, the flexible fiber optical cable couples light from a laser source or a LED to the photocathode.

U.S. patent application Ser. No. 09/884,561 and hereby incorporated by reference)(hereinafter the "'561" application) discloses an optically driven (for example, laser driven) x-ray source using a reduced-power, increased efficiency electron source, which generates electrons with minimal heat loss. The '561 application discloses the use of laser energy to heat an electron emissive surface of a thermionic emitter, instead of using an electric current to ohmically heat an electron emissive surface of a thermionic emitter. With the optically driven thermionic emitter, electrons can be produced in a quantity sufficient to produce the electron current necessary for generating therapeutic radiation at the target, while significantly reducing the requisite power requirements.

Even though the above-discussed miniature radiation sources can generate x-rays local to the target tissue, it is difficult to provide a uniform, or other desired, dose of radiation to an irregularly shaped target tissue, using these radiation sources. In one form, these radiation sources generally act as point sources of therapeutic radiation. The intensity of the radiation from a point source decreases uniformly with approximately the square of the distance (R) from the source (i.e., $1/R^2$). Since body cavities, or the beds of resected tumors, are not generally spherically symmetrical, a point source within a body cavity or central to the resected tumor bed will not deliver a uniform dose of radiation to the tissue lining of the cavity or bed. Similarly, for a non-spherical tumor, a point source at the tumor center will not deliver radiation with an isodose contour matching the peripheral surface of the tumor. U.S. Pat. No. 5,422,678 to Dinsmore et al. (the "'678 patent") discloses an x-ray source which allows the x-ray target to emit x-rays in a predetermined spectral range, by providing a beam steering assembly that controls the focus and deflection of the electron beam incident on the target. The beam steering assembly includes means for sensing the deflection of the electron beam, by monitoring the back-scattered x-rays, i.e. the x-rays emitted from the target in a backward direction along the path of the electron beam. A feedback signal is generated in response to the sensed deflection. The feedback signal is provided to an electron beam deflection controller, which controls the electron beam in response to the feedback signal.

In U.S. Pat. No. 5,422,926 to Smith et al. (the "'926 patent")(commonly owned by the assignee of the present application, and hereby incorporated by reference), an x-ray source is disclosed that is adapted for irradiating a volume in accordance with a predetermined dose distribution. In the '926 patent, a variable thickness x-ray shield is disclosed, which allows the irradiation of a preselected volume, defined by a set of isodose contours. This type of shielding around the x-ray target, or at the emission site, enables control of the energy and spatial profile of the x-ray emission, to match the preselected distribution of radiation throughout the deisred region.

The treatment regions within a patient's anatomical structure, however, are usually not adapted for uniform or predefined patterns of irradiation, because the organs or body cavities generally have arbitrary and irregular shapes and geometries. Cancerous tumors are also usually shaped irregularly, and are distributed randomly across a given anatomical region. A spherically isotropic spatial distribution of therapeutic radiation may not be suitable in many cases, for such arbitrarily and irregularly shaped treatment regions. The areas of a patient's body requiring treatment may be characterized by twists and bends. In some cases, the geometry of the target region may not be fixed, in the bladder for example, which has a flexible inner wall without a well-defined shape. Also, some treatment procedures may require delivery of localized radiation to portions of the human body that are not easily accessible.

Accordingly, there is a need for a system that permits the surgeon or technician to monitor in real time the delivered dose of therapeutic radiation during the treatment procedure. Such a system would enable the surgeon to regulate the generation and delivery of the therapeutic radiation, in response to the monitored dosage, thereby more accurately deliver therapeutic radiation to a treatment region, as compared to a system in which radiation is delivered according to a pre-planned radiation treatment profile.

SUMMARY

The present invention relates to a therapeutic radiation source, for example a miniaturized x-ray source, that includes an in-situ radiation detecting system for monitoring in real time the amount of therapeutic radiation generated by the source. The radiation detecting system generates a signal representative of the generated radiation, i.e. representative of the dosage of the delivered radiation. The radiation detecting system therefore allows the physician to monitor the cumulative dosage of the radiation being delivered during the treatment procedure, and to adjust the intensity of the delivered radiation according to his desired dosage distribution profile.

The therapeutic radiation source, which in a preferred embodiment is an x-ray source, includes a probe assembly. The probe assembly includes an optical delivery structure, such as a fiber optic cable, enclosed within an outer sheath or catheter, that may be flexible. The fiber optic cable is adapted for transmitting optical radiation, incident on an proximal end of the cable, to a distal end of the cable. An optical source, such as a laser source or other high intensity light source, generates light that is directed to the proximal end of the fiber optic cable, causing that light to propagate to the distal end. A radiation generator assembly is coupled to the distal end of the fiber optic cable. The radiation generator assembly includes, within an x-ray transmissive, evacuated capsule, an electron source at one end and a target element at another end. The electron source is in optical communication with the fiber optic cable. The electron source emits electrons in response to light that is transmitted to the distal end of the fiber optic cable and that is incident on the electron source. In one exemplary embodiment of the invention, the electron source is a laser-heated thermionic cathode. In another embodiment of the invention, the electron source is a photocathode.

The target element includes an x-ray emissive material, such as gold or tungsten, facing the electron source. An accelerating voltage is provided between the electron source and the target element, so as to establish an accelerating electric field that acts to accelerate electrons emitted from the electron source toward the target element. The target element emits x-rays in response to incident accelerated electrons from the electron source.

In the present invention, an in situ radiation detecting system enables real time monitoring of the amount of the x-rays emitted by the target element. The radiation detecting system includes a scintillator material disposed along a path of a portion of the x-rays emitted by the target element. The scintillator generates light in response to the emitted x-rays that are incident thereon. The intensity of the scintillator light is proportional to the energy deposited within the scintillator material by the incident x-ray photons. A photodetector is in optical communication with the scintillator material, and converts the scintillator light incident thereon into a signal indicative of the intensity of the x-ray radiation that strikes the scintillator material. This signal is representative of the total radiation flux emitted by the target element.

In a preferred embodiment of the invention, the in-situ radiation detecting system preferably includes a feedback controller. The feedback controller typically includes a feedback circuit and a controller. The feedback circuit sends the indicative signal from the photodetector to the controller. The controller includes a processor for calculating, in response to the indicative signal, a cumulative dosage of the emitted therapeutic radiation. The controller also includes intensity control circuitry for controlling the intensity of the emitted x-rays, and duration control circuitry for controlling the duration of the emission of the x-rays.

The feedback controller may also include a display unit, which allows real time visual monitoring of the therapeutic radiation emitted by the target element and delivered to a treatment region. By way of example, the controller may generate a "synthetic" image, in which a issue is "painted" in real time with colored regions, where different colors represent different radiation dose levels.

DETAILED DESCRIPTION

Figure 1:
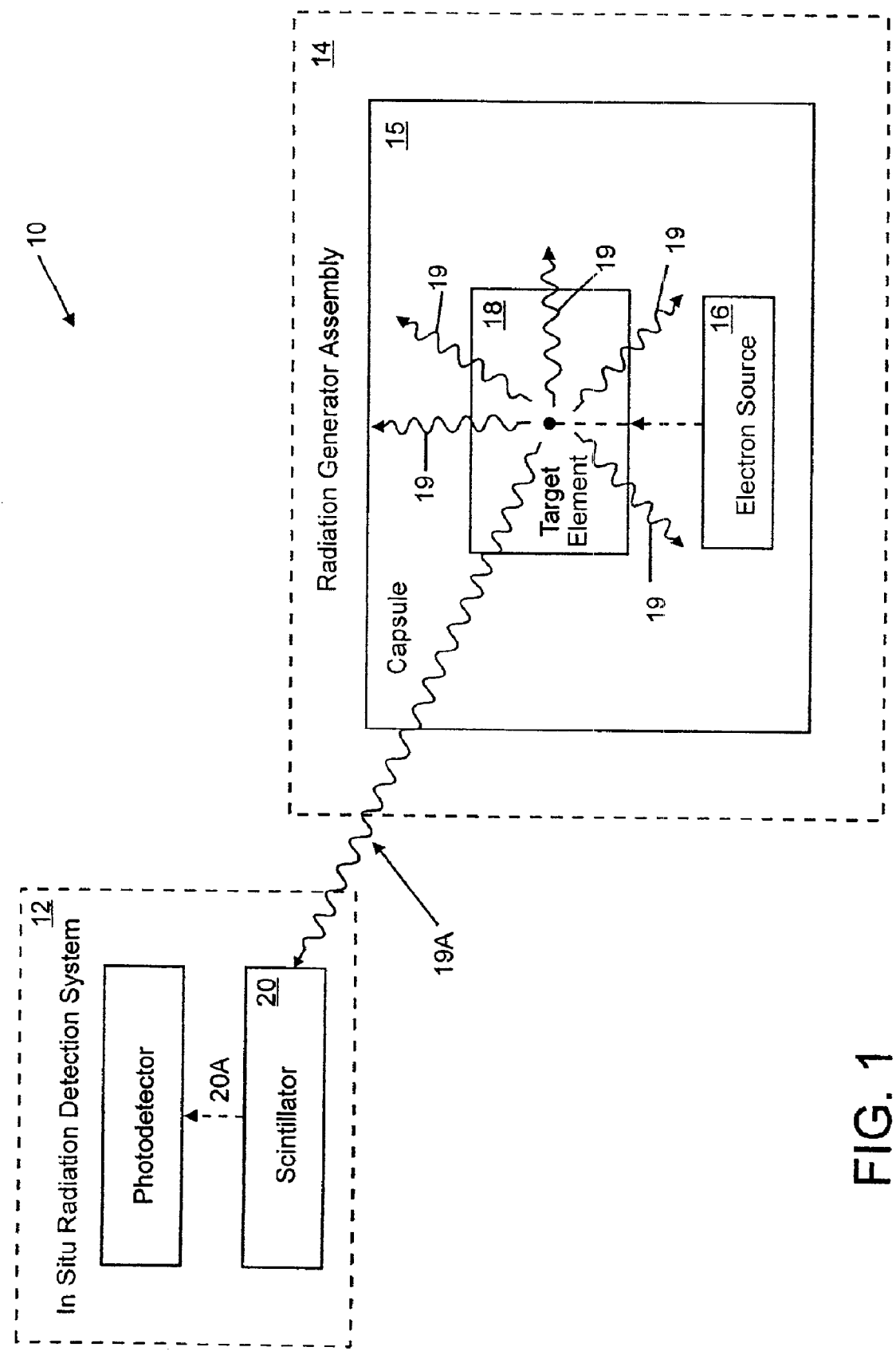
FIG. 1 is a schematic block diagram of one embodiment of an apparatus in accordance with the present invention.

FIG. 1 is a schematic block diagram of a therapeutic radiation source 10, constructed in accordance with the present invention and including an in situ radiation detection system 12. The therapeutic radiation source 10 includes a radiation generator assembly 14 having an electron source 16, and a target element 18 adapted to emit therapeutic radiation 19 in response to incident accelerated electrons from the electron source 16. The electron source 16 and the target element 18 are enclosed within an evacuated capsule 15. The in situ radiation detecting system 12 monitors in real time the amount of therapeutic radiation 19 emitted by the target element 18. In a preferred embodiment, the therapeutic radiation 19 are x-rays, although the scope of this invention is not limited to x-rays. The in situ radiation detecting system 12 includes a scintillator 20 disposed along a path of a portion (19A) of the emitted therapeutic radiation. The scintillator 20 emits scintillator light 20A in response to the x-rays 19A that are emitted by the target element 18 and that are incident on the scintillator 20. A photodetector 22 is in optical communication with the scintillator 20. The photodetector 22 provides a signal indicative of the intensity of the emitted therapeutic radiation that is incident upon the scintillator 20.

Figure 2A:
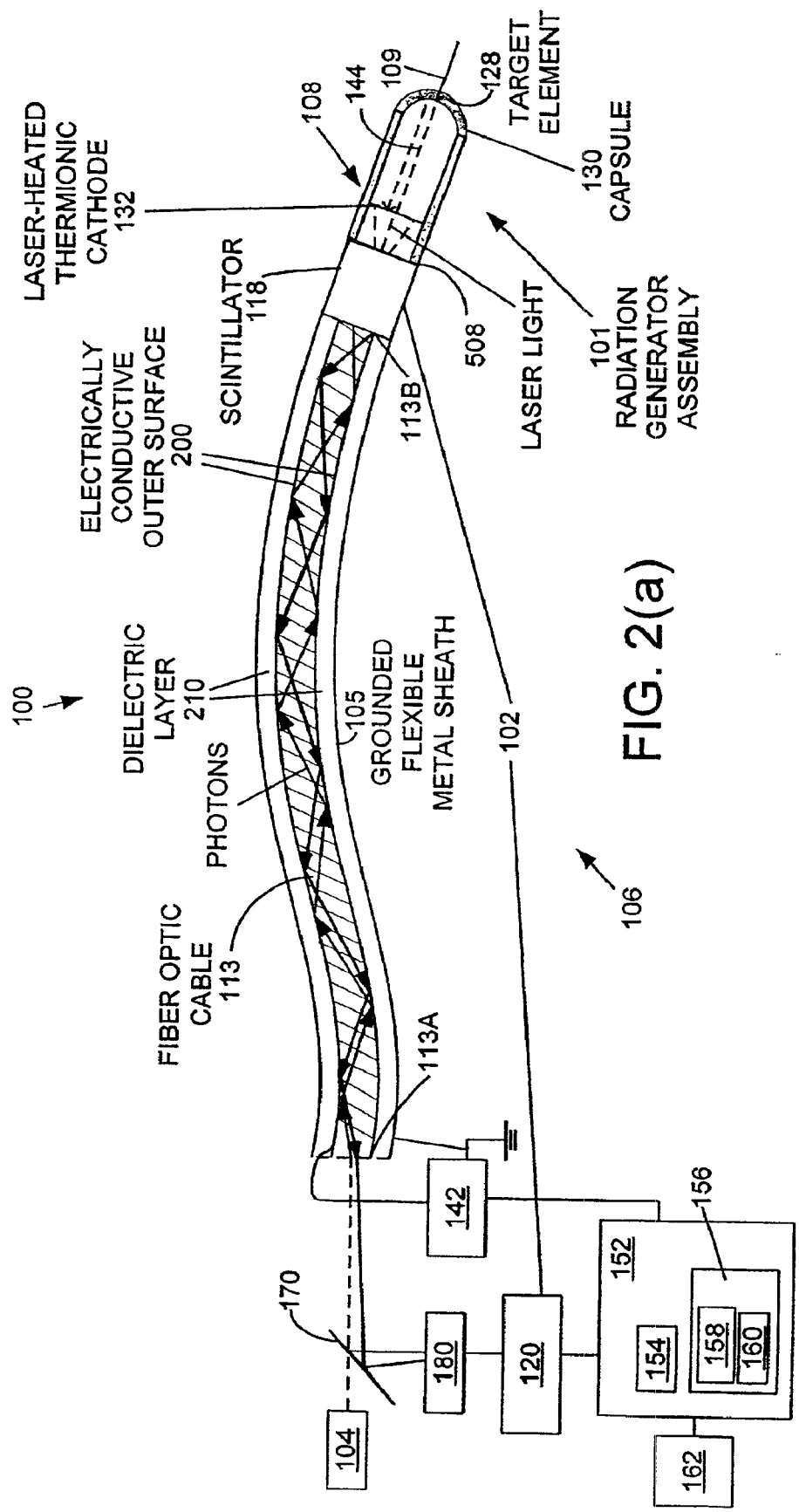
FIG. 2(a) provides an illustration of one embodiment of the present invention, in which an x-ray source having a laser-driven thermionic cathode is provided with an in situ radiation detection system.

FIG. 2(a) provides a more detailed illustration of one embodiment of the present invention, in which a miniature, laser-driven x-ray source 100 is provided with an in situ radiation detection system 102. The miniature, laser-driven x-ray source 1,00 shown in FIG. 2(a) includes an optical source. 104 and a probe assembly 106. The probe assembly 106 includes optical delivery structure 113, such as a fiber optic cable 113. In the illustrated embodiment, an electrically conductive sheath 105 is disposed about the fiber optic cable 113. A radiation generator assembly 101 is coupled to the distal end of the probe assembly 106, and includes an electron source 108 for generating electrons, and a target element 128. The electron source 108 and the target element 128 are enclosed within an evacuated capsule 130. A high voltage power supply 142 provides an accelerating voltage between the electron source 108 and the target element 128. The target element 128 includes at least one x-ray emissive material that emits x-rays, in response to accelerated electrons from the electron source 108. A scintillator 118 and a photodetector 120 are arranged so as to provide in-situ x-ray detection.

The probe assembly 106 includes an optical delivery structure 113 having a proximal end 113A and a distal end 113B. In the illustrated embodiment, the optical delivery structure 113 is enclosed within a flexible, electrically conductive catheter 105, although a rigid probe may be used in other embodiments of the invention. The distal end 113B of the optical delivery structure 113 is coupled to the radiation generator assembly 101. In a preferred embodiment, the optical delivery structure 113 is a flexible fiber optic cable extending from the proximal end 113A to the distal end 113B. As well known in the art, the fiber optic cable 113 is adapted to transmit optical radiation that is incident on the proximal end 113A of the fiber optic cable 113 to the distal end 113B thereof, by total internal reflection. Although an optical fiber is used in this preferred embodiment, other forms of the invention may use other optical delivery structures, such as dielectric mirrors, in order to direct optical radiation therethrough.

In the illustrated embodiment, the flexible catheter 105 that encloses the fiber optic cable 113 is a small-diameter, flexible metallic outer sheath. The fiber optic cable 113 may also include an electrically conductive outer surface 200. For example, the outer surface of the fiber optic cable 113 may be made conductive by applying an electrically conductive coating. The electrically conductive outer surface 200 of the fiber optic cable 113 can provide a connection to the electron source 108 from the high voltage power supply 142.

In one embodiment of the invention, the radiation-generator assembly 101 may also have an electrically conductive outer surface. Preferably, both the flexible metallic sheath 105 and the outer conductive surface of the radiation generator assembly 101 are set at ground potential, in order to reduce the shock hazard of the device. The flexible sheath 105 couples a ground return from the target element 128 to the high voltage power supply 142, thereby establishing a high voltage field between the electron source 108 and the target element 128. In an exemplary embodiment, the fiber optic cable 113 may have a diameter of about 200 microns, and the flexible metallic sheath 105 may have a diameter of about 1.4 mm, although other sizes may be used in other embodiments of the invention. A layer 210 of dielectric material may provide insulation between the outer surface of the fiber optic cable 113 and the inner surface of the metallic sheath 105.

The optical source 104 includes means for generating a beam of optical radiation directed to the proximal end 113A of the optical delivery structure 113. In a preferred embodiment, the optical source 104 is a laser source 104 that generates a substantially monochromatic and coherent beam of laser light, although in other embodiments of the invention, other sources of high intensity light, such as LEDs (light emitting diodes) may be used. The laser 104 may be adiode laser, by way of example. Other lasers known in the art may be used, including but not limited to Nd:YAG lasers, Nd:YVO$_4$ lasers, molecular lasers, and solid state lasers. When activated, the laser 104 generates a beam of laser light directed to the proximal end 113A of the optical delivery structure 113.

The radiation generator assembly 101 includes the electron source 108, and the target element 128. The radiation generator assembly 101, which in one embodiment may be about 0.5 cm to about 2 cm in length, extends from the distal end of the probe assembly 106, and includes a shell or capsule 130 that encloses the electron source 108 and the target element 128. According to one embodiment, the capsule 130 is rigid in nature and generally cylindrical in shape. In this embodiment, the cylindrical capsule 130, enclosing the other elements of the radiation generator assembly 101, can be considered as providing a substantially rigid housing for the electron source 108 and for the target element 128. The capsule 130 defines a substantially evacuated interior region along a reference axis 109, between the electron source 108 at a proximal end of the capsule 130 and an x-ray transmissive window at a distal end of the capsule 130. The capsule 130 may be made of an x-ray transparent glass or ceramic material, by way of example. Preferably, the wall of the radiation generator assembly 101 is an electrical insulator, while the external surface of the assembly 101 is electrically conductive. According to one embodiment of the invention, the radiation generator assembly 101 is hermetically sealed to the distal end of the probe assembly 106, and evacuated. According to another embodiment of the invention, the probe assembly 106 is hollow, and the probe assembly 106 and the radiation generator assembly 101 are evacuated.

In the embodiment illustrated in FIG. 2(a), the electron source 108 is a thermionic cathode 132 having an electron emissive surface facing the target element 128. As known in the art, electrons are emitted from the electron emissive surface of the thermionic cathode 132 into the surrounding vacuum, when the surface is heated to a sufficient temperature. The electrons are emitted with a Maxwellian distribution of velocities corresponding to the cathode temperature. In a preferred form, the thermionic cathode 132 is disc shaped, but may have other shapes as disclosed in related U.S. application Ser. No. 09/884,229 and hereby incorporated by reference)(hereinafter the "'229 application"). A disc shaped cathode may be held in place by swage of the end or by laser welding. The thermionic cathode 132 may be formed of a metallic material, including tungsten, thoriated tungsten, other tungsten alloys, and tantalum. In one embodiment, the cathode 132 may be formed by depositing a layer of electron emissive material on a base material, so that an electron emissive surface is formed thereon. By way of example, the base material may be formed from one or more metallic materials, including but not limited to Group VI metals such as tungsten, and Group II metals such as barium. In one form, the layer of electron emissive material may be formed from materials including, but not limited to, aluminum tungstate and scandium tungstate. The thermionic cathode 132 may also be an oxide coated cathode, where a coating of the mixed oxides of barium and strontium, by way of example, may to applied to a metallic base, such as nickel or a nickel alloy.

Grids or support coils (not shown), consisting of spirals of wire surrounding the cathode 132, may be swaged or welded to the interior surface of the capsule 130 of the radiation generator assembly 101. Alternatively, the grids may be formed by photochemical etching techniques. The grids may be constructed from tungsten, molybdenum, or rhenium, by way of example, or may be formed from the cathode materials.

In the embodiment illustrated in FIG. 2(a), the x-ray source 100 also includes means 142 for providing an accelerating voltage between the electron source 108 and the target element 128 so as to establish an accelerating electric field which acts to accelerate electrons generated from the electron source 108 toward the target element 128. The means 142 for establishing an accelerating electric field includes, but is not limited to, a high voltage source, such as a high voltage power supply 142. In the illustrated embodiment, the high voltage power supply 142 provides a high potential difference across the conductive outer surface 200 of the fiber optical cable, and the metallic sheath 105, to establish an acceleration potential difference between the thermionic cathode 132 and the grounded target element 128. In this way, electrons emitted from the thermionic cathode 132 are accelerated toward the target element 128, and an electron beam is generated. The electron beam is preferably thin (e.g. 1 mm or less in diameter), and is established along a beam path 144, along the nominally straight reference axis 109, that extends to the target element 128. The target element 128 is positioned in the beam path. The distance from the thermionic cathode 132 to the target element 128 is preferably less than 2 mm.

The high voltage power supply 142 preferably satisfies three criteria: 1) small in size; 2) high efficiency, so as to enable the use of battery power; and 3) independently variable x-ray tube voltage and current, so as to enable the unit to be programmed for desired applications. Preferably, the power supply 142 is a programmable power supply 142 including selectively operable control means for selectively controlling the amplitude of the output voltage and the amplitude of the beam generator current. A high-frequency, switch-mode power converter is preferably used to meet these requirements. The most appropriate topology for generating low power and high voltage is a resonant voltage converter working in conjunction with a high voltage, Cockroft-Walton-type multiplier. Low-power dissipation, switch-mode power-supply controller-integrated circuits (IC) are available for controlling such topologies with few ancillary components. A more detailed description of an exemplary power supply suitable for use as power supply 142 is provided, for example, in U.S. Pat. Nos. 5,153,900 and 5,428,658.

The target element 128 is preferably spaced apart from and opposite the electron emissive surface of the thermionic cathode 132, and has at least one x-ray emissive material adapted to emit x-rays in response to incident accelerated electrons from the cathode 132. In one embodiment, the target element 128 is a small beryllium (Be) substrate, coated on the side exposed to the incident electron beam with a thin film or layer of a high-Z element, such as tungsten (W), uranium (U) or gold (Au). As the atomic number of the x-ray emissive element increases, the peak output in the spectral distribution curve of the emitted x-rays, and the characteristic spectral lines of the x-rays, shift to higher energies. The efficiency of x-ray generation is highly dependent on the acceleration voltage provided by the high voltage power supply 142, although independent of the electron beam current. By way of example, when the electrons are accelerated to 30 keV-, a 2.2 micron thick tungsten layer absorbs substantially all of the incident electrons, while transmitting approximately 91% of any 30 keV-, 76% of any 20 keV-, and 67% of any 10 keV-x-rays generated in that layer. In this embodiment, the beryllium substrate is 0.5 mm thick. With this configuration, 95% of the x-rays generated in directions normal to and toward the beryllium substrate, and having passed through the tungsten layer, are then transmitted through the beryllium substrate and outward at the distal end of the probe assembly 106. While the target element 128 shown in FIG. 2(*a*) is in the-form of a hemispherical layer, other shaped elements may be used, such as those having disk-like or conical shapes. X-rays emitted from the target element 128 are directed through the x-ray transmissive window of the capsule 130 onto a desired region-to-be-treated.

In some forms of the target, the target element 128 may include a multiple layer film, where the differing layers may have different emission characteristics. By way of example, the first layer may have an emission peak at a relatively low electron energy, and the second, underlying layer may have an emission peak at a relatively high electron energy. With this form of the invention, a low energy electron beam may be used to generate x-rays in the first layer to achieve a first radiation characteristic, and high energy electrons may be used to penetrate through to the underlying layer to achieve a second radiation characteristic. As an example, a 0.5 mm wide electron beam is emitted at the cathode 132 and accelerated to 30 keV, with 0.1 eV transverse electron energies, and arrives at the target element 128, with a beam diameter of approximately the cathode area, at the target element 128. X-rays are generated in the target element 128 in accordance with pre-selected beam voltage, current, and target material composition. The x-rays thus generated pass through the beryllium substrate with minimized loss in energy. As an alternative to beryllium, the target substrate may be made of carbon or other suitable material which permits x-rays to pass with a minimum loss of energy. An optimal material for target substrate is carbon in its diamond form, since that material is an excellent heat conductor. Using these parameters, the resultant x-rays have sufficient energy to penetrate into soft tissues to a depth of a centimeter or more, the exact depth dependent upon the x-ray energy distribution.

The fiber optical cable 113 directs the beam of laser radiation, which has been transmitted therethrough, to impinge upon the electron emissive surface of the thermionic cathode 132. The beam of laser radiation must have a power level sufficient to heat at least a portion of the electron emissive surface to an electron emitting temperature so as to cause thermionic emission of electrons from the surface. It has been found that only a few watts of power is needed to generate over 100 $\mu$A of electron current, using a Nd:YAG laser coupled into a $SiO_2$ optical fiber having a diameter of 400 microns. In another example, an infrared diode laser was used to achieve about 100 $\mu$A of electron current with only 180 mW of power. The laser beam rapidly heats the surface of the cathode 132 to an electron emitting temperature, below the melting point of the metallic cathode 132. When the surface reaches an electron emitting temperature, electrons are thermionically emitted from the surface into the vacuum provided by the capsule 130. The high voltage field between the cathode 132 and the target element 128 accelerates these electrons, thereby forcing them to strike the surface of the target element 128 and emit x-rays.

In an alternative embodiment, illustrated in FIG. 2(*b*), the x-ray source 100 includes a photocathode 150, rather than a laser-driven thermionic cathode 132. The photocathode 150 has a photoemissive surface coated with a semitransparent photoemissive substance, such as Ag—O—Cs. In this embodiment, the laser beam shining down the fiber optic cable 113 activates the transmissive photocathode 150 which generates free electrons by the photoelectric effect. The high voltage field between the cathode 132 and the target element 128 accelerates these electrons, thereby forcing them to strike the surface of target element 128 and produce x-rays.

A photocathode must have sufficient quantum efficiency, where quantum efficiency relates to the number of electrons generated per incident light quantum. The degree of efficiency must be balanced to the intensity of available incident light. In order to generate, for example, 20 $\mu$A of current from a Ag—O—Cs photocathode 150 using a laser that emits light at a wavelength of 0.8 $\mu$m, the 0.4% quantum efficiency of the photocathode 150 for this wavelength requires that the laser emits 7.5 mW optical power. Such diode lasers are readily commercially available. According to this embodiment, the photoemissive surface which forms the photocathode 150 can, in fact, be quite small. For example, for a current density at the photocathode 150 of 1 A per $cm^2$, the photoemitter's diameter need only be approximately 50 $\mu$m.

In the above embodiments, the probe assembly 106, along with the radiation generator assembly 101, can be coated with a biocompatible outer layer, such as titanium nitride on a sublayer of nickel. For additional biocompatibility, a sheath of, for example, polyurethane can be fitted over the catheter 105.

The radiation detection system 102, illustrated in both FIGS. 2(*a*) and 2(*b*), allows real time monitoring of the emitted x-rays. A scintillator 118 is disposed along a path of a portion of the emitted x-rays. The scintillator 118 is adapted to generate flashes of scintillator light, in response to the x-rays that are incident thereon. As well known, the incident x-rays passing through the scintillator 118 interact with the scintillator material, causing excitations. Various types of interactions may cause these excitations. For instance, an x-ray photon may collide with a bound electron, imparting its energy to the electron. Bound electrons in the valence band of the scintillator material are thus excited into the conduction band. As these excited electrons return to the valence band, some of them generate photons that manifest themselves as flashes of scintillator light. The number of photons of scintillator light that are produced, i.e. the intensity of the scintillator light, is proportional to the total energy deposited in the scintillator by the x-ray photons, i.e. to the quantity of the incident x-ray photons, as well as the energies of the individual x-ray photons.

In the embodiments illustrated in FIGS. 2(*a*) and 2(*b*), the scintillator 118 is affixed to the distal end 113B of the fiber optic cable 113. In this embodiment, the scintillator 118 is thus arranged so that the x-rays incident on the scintillator 118 are predominantly those x-rays that are emitted from the target element 128 in a backward direction, with respect to the path 144 of the incident electron beam. It should be noted, however, that configurations that place the scintillator 118 along any path of any portion of the emitted x-rays are within the scope of this invention. In this exemplary embodiment, a hole in the cathode 132 permits passage of these "back-scattered" x-rays through the cathode 132 and onto the scintillator 118.

Scintillators are typically made of transparent crystalline materials, or plastics, or glass. Crystalline materials may include inorganic crystals such as NaI(Tl) (sodium iodide crystals doped with a small amount of thallium) and YAP:Ce (yittrium aluminum perovskite, doped with cerium), or terbium-doped glass fiber. Scintillators made of a polymer material, i.e. plastics such as polstyrene, are generally cheaper, however because of the heat-generating laser beam, scintillators made of crystals or glass are preferable.

In the illustrated embodiment, a photodetector 120 is placed in optical communication with the scintillator 118.

This optical communication may be through the same optical fiber as the laser power delivery fiber, or a separate fiber. The photodetector 120 converts the scintillator light into a signal proportional to the intensity of the scintillator light, and hence indicative of the intensity of the x-rays emitted by the target element 128 and incident on the scintillator 118. The photodetector 120 may be a photomultiplier, by way of example. As known in the art, a scintillator photon incident on the photocathode of the photomultiplier 120 releases electrons, which are accelerated and focused onto successive dynodes, releasing secondary electrons in greatly increasing numbers. After successive multiplicative stages, even a few incident x-ray photons produce a measurable pulse at the output of the photomultiplier 120. The height of the pulse is proportional to the energy of the incident x-ray photons, and the number of pulses is proportional to the intensity of the incident x-rays. The photodetector 120 thus produces an electric signal indicative of the intensity of the emitted x-rays that impinge upon the scintillator 118.

Figure 2B:
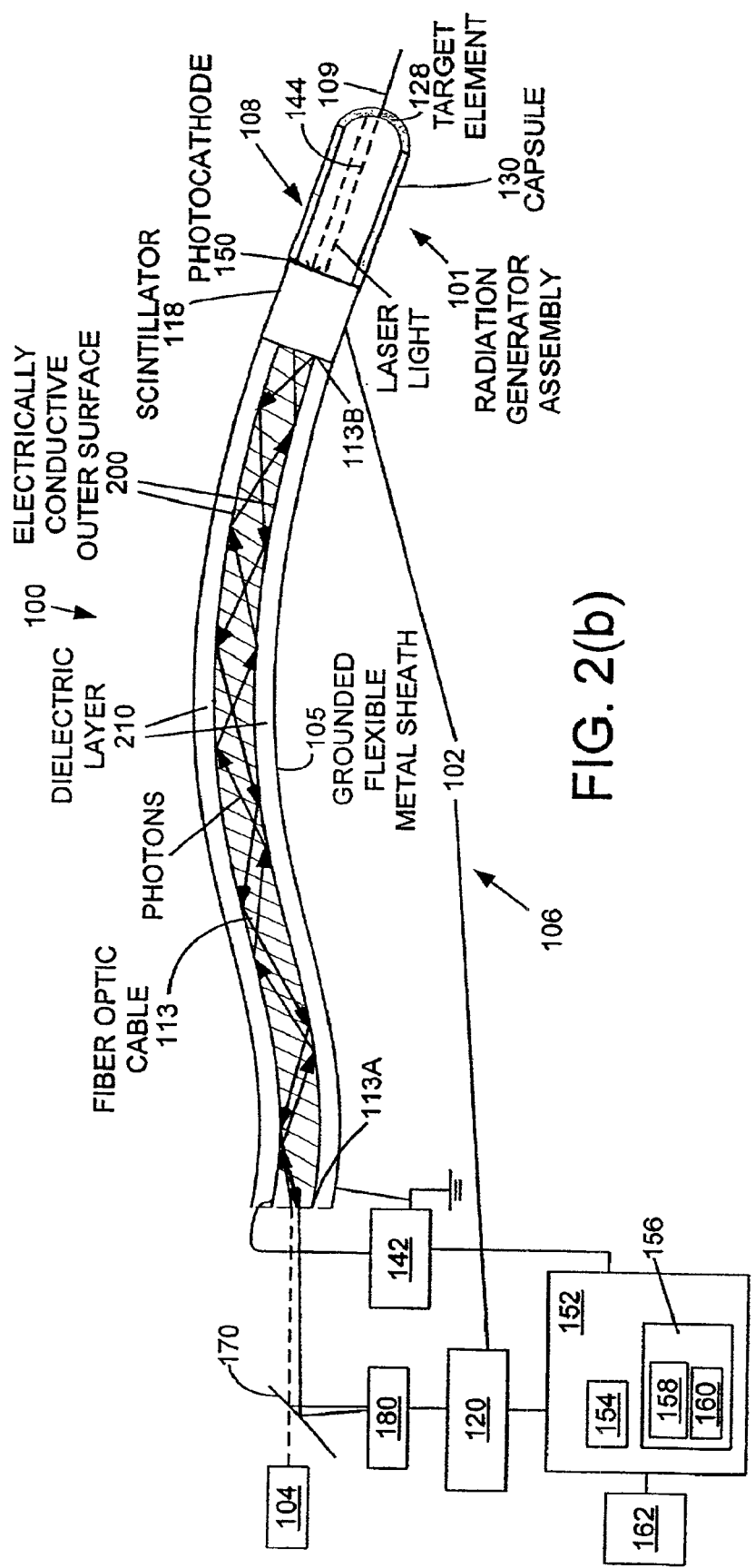
FIG. 2(b) provides an illustration of another embodiment of the present invention, in which an x-ray source having a photocathode is provided with an in situ radiation detection system.

The radiation detection system 102 may include an optical system for selectively directing light so that only light from the scintillator 118 is incident on the photodetector 120, and all other types of optical radiation, such as ambient visible light and light from the laser source 104, are filtered out. In one embodiment, the optical system may include a dichroic beam splitter 170, and a bandpass filter 180. The dichroic beam splitter 170 and the filter 180 are disposed between the optical source 104 and the fiber optic cable 113, as shown in FIGS. 2(a) and 2(b). The filter 180 may be a 350 nm filter, or a 808 nm filter, by way of example.

Alternatively, an absorbing material such as the Nd:YVO$_4$ laser material may be used instead of a bandpass filter, or may be used together with a bandpass filter to complement the filter. In such an embodiment of the invention, the optical source. 104 is a diode laser, which has a 808 nm output wavelength. It is known that the laser material in a Nd:YVO$_4$ laser crystal has an extremely high absorption coefficient at exactly the output wavelength of the diode laser, namely 808 nm. Also, the Nd:YVO$_4$ laser material is uniform, and has no structure that would allow pin-hole type defects that would cause photons to leak through, as frequently occurs with thin film type optical filters. Because a Nd:YVO$_4$ laser crystal is extremely absorptive at the pump frequency, and quite transmissive at the scintillator frequency, the Nd:YVO$_4$ laser material is an extremely effective filter. A 1 mm thick Nd:YVO$_4$ material absorbs virtually all of the incident laser light. The Nd:YVO$_4$ material can advantageously be used in combination with another type of filter, such as a regular thin film optical filter.

The photodetector 120 is preferably coupled to a feedback controller 152 that permits real time monitoring of the intensity and duration of the emitted x-rays. The feedback controller 152 includes a feedback circuit 154 and a controller 156. The feedback circuit 154 feeds the indicative signal from the photodetector 120 back to the controller 156. The controller 156 includes intensity control circuitry 158 for controlling the intensity of the emitted x-rays, and duration control circuitry 160 for controlling the duration of the emission of x-rays.

Figure 3A:
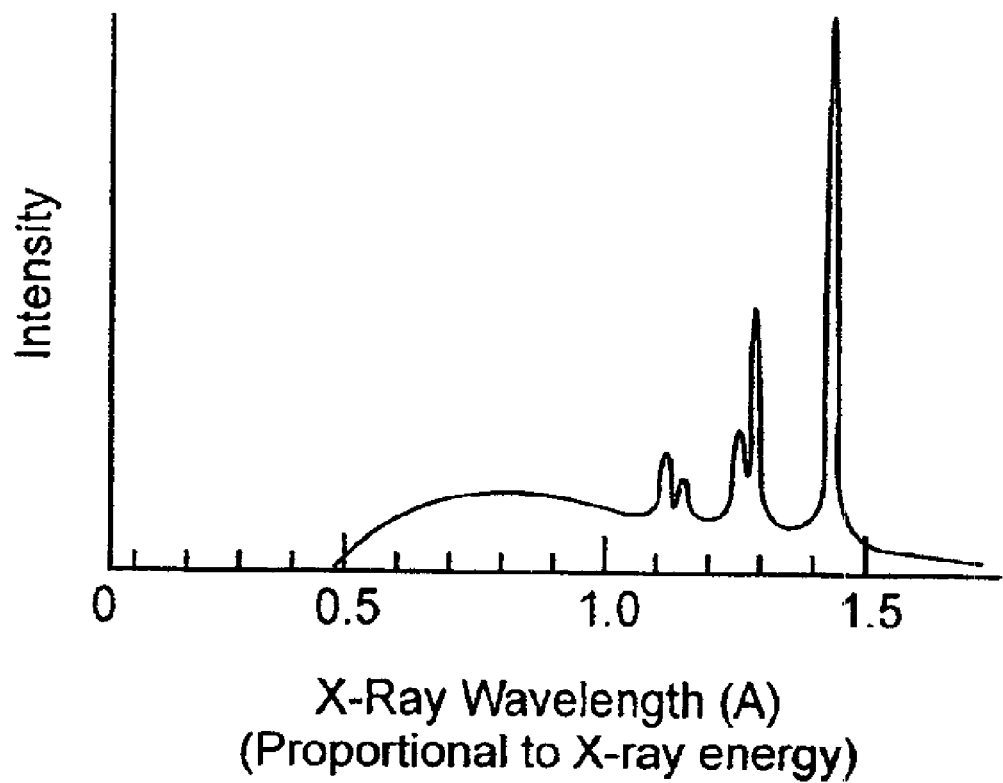
FIG. 3(a) illustrates an x-ray spectrum for a tungsten target that includes the continuous bremsstrahlung spectrum as well as the characteristic spectral lines for tungsten.

The intensity and spectral distribution of the emitted x-rays depend, inter alia, on the magnitude of the electron beam current generated by the thermionic cathode 132, and on the accelerating voltage that accelerates the beam of electrons striking the target. This is because x-rays are produced when the incident electrons, interacting with the target nuclei, are decelerated and eventually brought to rest. FIG. 3(a) illustrates an exemplary x-ray spectrum, for a tungsten target. As seen in FIG. 3(a), the illustrated spectrum consists of a continuous bremsstrahlung ("braking") spectrum, and characteristic x-ray spectral lines for tungsten. Bremsstrahlung radiation occurs because an electron, having some initial kinetic energy, is decelerated during an encounter with a heavy target nucleus. The Coulomb interaction between the electron and the nucleus causes the deceleration. The decelerating electron causes the appearance of x-ray bremsstrahlung photons, whose energies correspond to the energy lost by the colliding electron. An electron in the incident beam typically loses different amounts of energy in many such encounters with the target nucleus, before the electron is finally brought to rest. The x-rays produced by numerous electrons making a large number of different encounters therefore produce many discrete x-ray photons having continuously varying wavelengths, i.e. a continuous bremsstrahlung spectrum is produced.

The discrete spectral lines are-characteristic of the transitions between bound electron energy levels of the atoms forming the target element 128, as allowed by the selection rules. When an incident electron passes near an electron in an inner subshell of an atom while traveling through the atoms of the target material, the incident electron can impart enough energy to the inner subshell electron to remove it from its very negative energy level and eject it from the target atom, because of the Coulomb interaction between the incident electron and the inner subshell electron. The sudden absence of a very negative energy electron renders the target atom in a highly excited state. As the atom returns to its ground state, it emits a set of high frequency photons, which produce the characteristic x-ray line spectrum of the particular atom forming the target material.

Figure 3B:
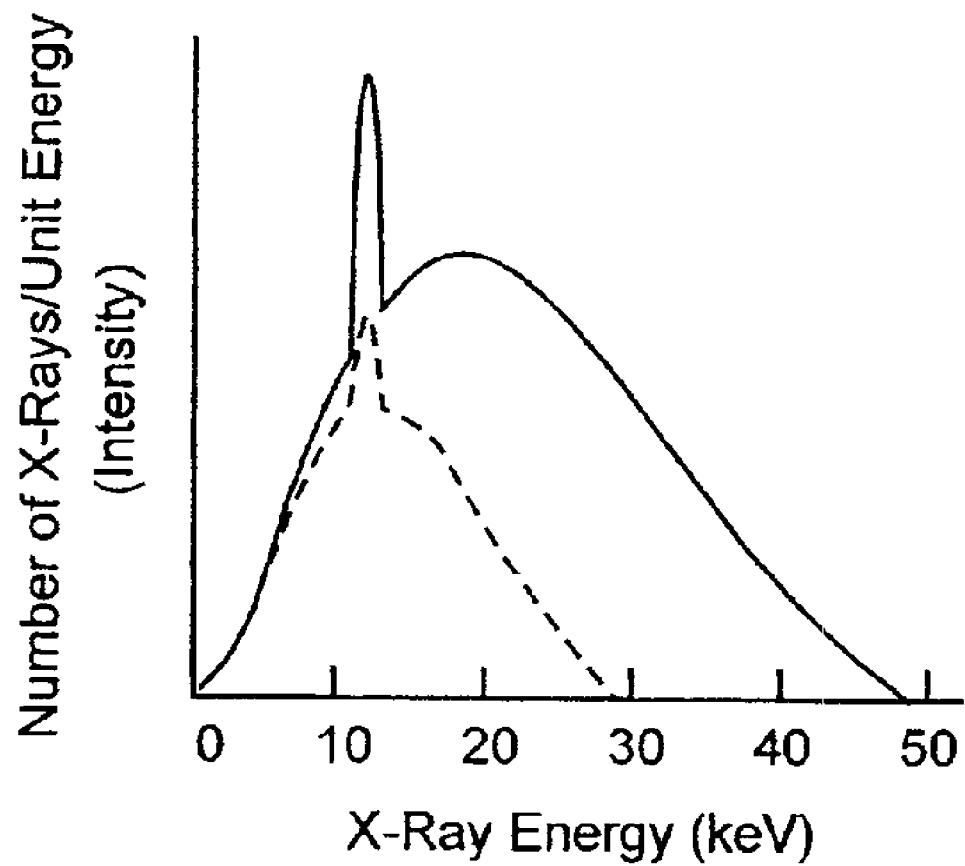
FIG. 3(b) illustrates the continuous bremsstrahlung x-ray spectrum emitted from a tungsten target for two different values of incident electron energy.

Increasing the electron beam current results in a directly proportional increase in x-ray emission at all energies. On the other hand, a change in the acceleration voltage results in a total x-ray output variation proportional to the square of the voltage. The change in the intensity spectrum of the x-rays, caused by a change in the acceleration voltage provided by the high voltage power supply 142, is illustrated in FIG. 3(b). FIG. 3(b) shows the x-ray emission spectra for a tungsten target, at two different acceleration voltages, namely 30 keV (dotted spectrum) and 50 keV (solid spectrum). As shown in FIG. 3(b), the intensity spectrum of the x-rays is a strong function of the acceleration voltage. Any change in the acceleration voltage between the cathode and the target results in a corresponding change in the speeds with which the electrons strike the target. As the electrons strike the target, their kinetic energy is transferred to the x-ray photons. A change in accelerating voltage thus results in a change in electron kinetic energy (proportional to the square of the electron speed), which in turn results in a corresponding change in the energies of the x-ray photons emitted by the x-ray source. As illustrated in FIG. 3(b), the change in the x-ray intensity spectrum resulting from a change in the acceleration voltage is proportional to the square of the voltage, and a corresponding shift in the peak x-ray photon energy occurs.

As seen from FIGS. 3(a) and 3(b), the x-ray intensity spectrum depends strongly on the magnitudes of the electron beam current and the accelerating voltage. Referring back to FIGS. 2(a) and 2(b), the intensity control circuitry 158 in the controller 156 controls the intensity of the emitted x-rays by controlling the magnitude of the accelerating voltage, and the magnitude of the electron beam current. The intensity control circuitry 158 may regulate the programmable power supply 142, in order to control the magnitude of the accelerating voltage provided by the power supply 142, and/or the magnitude of the electron beam current generated by the cathode 132. The intensity control circuitry 158 permits a user to vary the intensity of the emitted x-rays as desired, by varying the accelerating voltage and the electron beam current.

The duration control circuitry 160 controls the duration of the emission of the x-rays. The duration control circuitry 160 may regulate the programmable power supply 142 so as to selectively activate the power supply 142, thereby controlling the time during which the accelerating voltage is provided between the cathode 132 and the target 128. The duration control circuitry 160 may also selectively activate the laser source 104, i.e. selectively turn on or off the laser source 104, so as to effectively control the activation time as well as the duration of emission for the laser-driven x-ray source 100.

The controller 156 also includes a processor, which is responsive to the feedback signals from the photomultiplier, and which calculates in real time a cumulative dose of the x-rays detected by the scintillator. The calculations assume that the x-rays are emitted evenly in all directions, even though only a small portion (i.e. those x-rays that are emitted in a backward direction relative to the incident electron beam) is detected by the scintillator 118. The calculated cumulative dose information may be displayed on a display unit 162, such as a monitor screen. This permits a surgeon or other radiotherapy professional to keep track of the cumulative dose of x-rays that he has delivered, while performing the medical procedure. The surgeon may perform real time visual monitoring of the x-rays emitted by the target element 128 and delivered to a treatment region. In one embodiment, the surgeon may generate a synthetic image, in which a displayed image of the target tissue is "painted" in real time with colored regions, where the various colors represent corresponding radiation dose levels.

By visualizing in real time the cumulative amount of x-ray radiation he has delivered, the surgeon can adjust the amount of radiation being delivered according to a desired dosage distribution. By means of the intensity control circuitry 158 and the duration control circuitry 160, the surgeon can control the amount of x-ray radiation being delivered at any point in time during the medical procedure.

Figure 4:
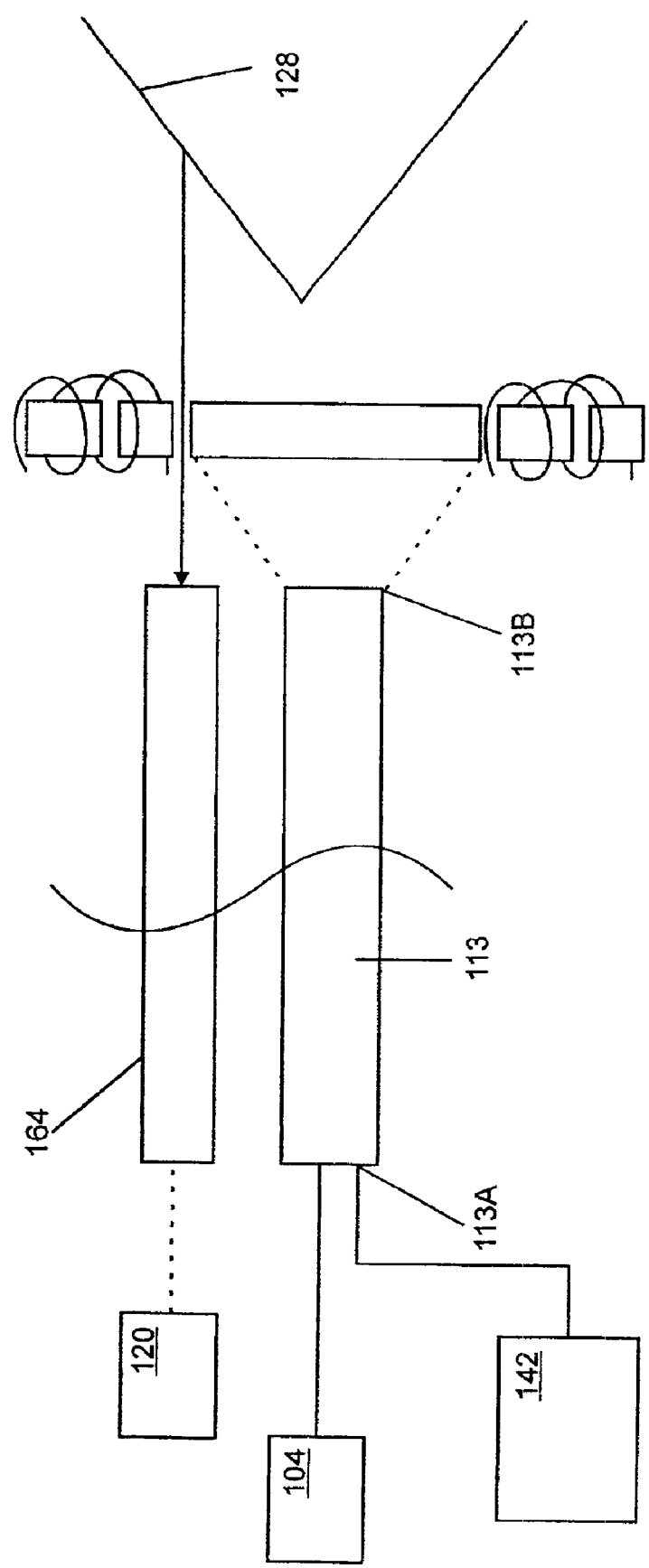
FIG. 4 illustrates one embodiment of the present invention in which the scintillator is an optical fiber made of scintillating material and is attached to the fiber optic cable that directs light from the laser to the electron source.

FIG. 4 illustrates another embodiment of the present invention in which the scintillator 118 in the radiation detecting system 102 is a second optical fiber 164, in addition to the fiber optic cable 113 that transmits the input laser light from its proximal end 113A to its distal end 113B. This second optical fiber 164 is formed of a scintillating material, which may be any of the scintillator materials discussed above. In this embodiment, the scintillating fiber 164 is attached to the first optical fiber 113. The scintillating fiber 164 may be glued to the first optical fiber 113 by suitable bonding means. The x-rays that reach the scintillating fiber 164 are thus emitted from the target element 128 and travel in a substantially backward direction relative to the path of the incident electron beam, passing through support coils 166. The scintillating fiber 164 preferably has an opaque coating, so as to prevent ambient visible light from introducing intensity measurement errors.

In an alternative embodiment (not shown) of the invention, the input fiber optic cable can itself function as a scintillator for detecting x-ray radiation emitted by the target element. In other words, the fiber optic cable that serves as an optical delivery structure for delivering input laser light to the electron source can also function as a scintillator for an in situ radiation detection system. In this embodiment, the input fiber optic cable is made of a scintillating material, which may be any of the scintillating materials described earlier. The x-rays that reach the scintillating fiber are the x-rays which travel in a backward direction relative to the path of the incident electron beam, after being emitted by the target element. In this embodiment, the cathode has a hole which permits passage of the back-scattered x-rays through the cathode and onto the scintillating fiber.

Figure 5:
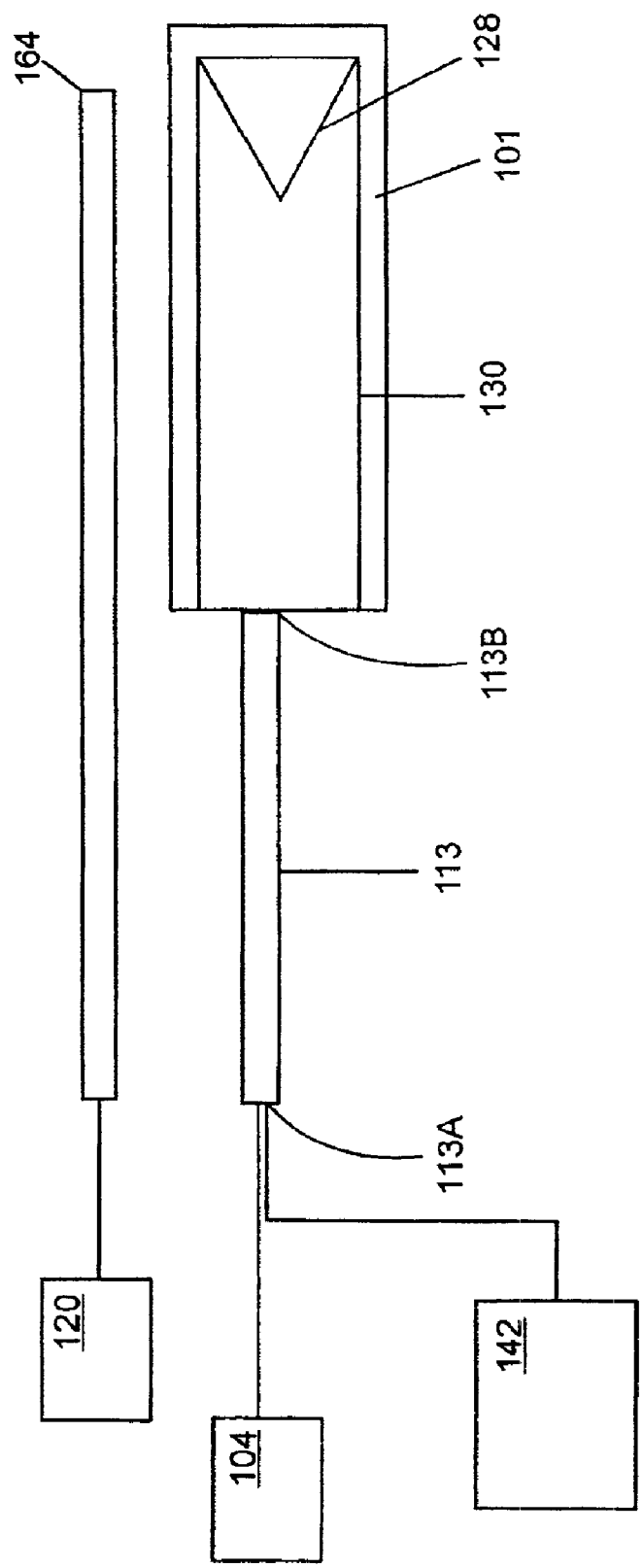
FIG. 5 illustrates one embodiment of the present invention in which the scintillator is an optical fiber made of scintillating material, and is disposed outside of the x-ray generator assembly.

FIG. 5 illustrates yet another embodiment of the present invention, in which the scintillator 118 in the radiation detecting system 102 is a scintillating fiber 164 that is disposed outside the radiation generator assembly 101 and along a path of a portion of the x-rays emitted from the target 128. As in the embodiment illustrated in FIG. 4, the scintillating fiber 164 is preferably coated with an opaque material. An x-ray transmissive window in the wall of the housing 124 provides optical coupling of the scintillating fiber 164 to the x-ray target 128.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A therapeutic radiation source, comprising
A. a probe assembly including an optical delivery structure having a proximal end and a distal end, said optical delivery structure being adapted for transmitting optical radiation incident on said proximal end to said distal end;
B. an optical source, including means for generating a beam of optical radiation directed to said proximal end of aid optical delivery structure;
C. a radiation generator assembly coupled to the probe assembly, including:
a. an electron source, responsive to light transmitted to said distal end of said optical delivery structure, for emitting electrons; and
b. a target element including at least one radiation emissive material adapted to emit therapeutic radiation in response to incident electrons from said electron beam;
D. means for providing an accelerating voltage between said electron source and said target element so as to establish an accelerating electric field which acts to accelerate electrons emitted from said electron source toward said target element; and
E. an in situ radiation detecting system for monitoring an amount of the therapeutic radiation emitted by said target element, said radiation detecting system including:
a. a scintillator disposed along a path of the therapeutic radiation emitted by said target element and adapted to generate scintillator light in response to the therapeutic radiation incident thereon, wherein the intensity of said scintillator light is proportional to the intensity of said incident therapeutic radiation;
b. a photodetector in optical communication with said scintillator by way of said optical delivery structure, for converting said scintillator light into a signal indicative of the intensity of said incident therapeutic radiation.

2. A therapeutic radiation source according to claim 1, further including a feedback controller responsive to said indicative signal, the feedback controller including:
a. a controller including processing means for calculating a cumulative dosage of said therapeutic radiation, and control means for controlling the intensity and duration of the emitted therapeutic radiation; and b. a feedback circuit for feeding back said indicative signal to the controller.

3. A therapeutic radiation source according to claim 2, wherein said control means comprises intensity control circuitry for controlling the intensity of the emitted therapeutic radiation, and duration control circuitry for controlling the duration of the emitted therapeutic radiation; and further wherein said intensity control circuitry comprises programmable means for user-controlled adjustment of at least one of the magnitude of said accelerating voltage and the magnitude of the current formed by said electron beam.

4. A therapeutic radiation source according to claim 3, wherein said duration control circuitry comprises means for selectively activating said optical source.

5. A therapeutic radiation source according to claim 3, wherein said duration control circuitry comprises means for selectively activating said means for providing an accelerating voltage.

6. A therapeutic radiation source according to claim 1, wherein said feedback controller includes a display unit, so as to allow real time visual monitoring of the therapeutic radiation emitted by said target element and delivered to a treatment region.

7. A therapeutic radiation source according to claim 6, wherein said display unit is operable to display a plurality of colors that represent a corresponding plurality of radiation doses delivered to said treatment region.

8. A therapeutic radiation source according to claim 1, wherein said therapeutic radiation includes x-rays.

9. A therapeutic radiation source according to claim 1, wherein said optical source is a laser source, and wherein said beam of optical radiation is substantially monochromatic and coherent.

10. A therapeutic radiation source according to claim 1, wherein said laser source is selected from the group consisting of a diode laser, a molecular laser and a solid state laser.

11. A therapeutic radiation source according to claim 1, wherein said scintillator is affixed to said distal end of said optical delivery structure.

12. A therapeutic radiation source according to claim 1, wherein said radiation detection system further includes an optical system for selectively directing light so that only said scintillator light is incident upon said photodetector, the optical system being adapted for separating said scintillator light from ambient visible light and from optical radiation generated by said optical source.

13. A therapeutic radiation source according to claim 12, wherein said optical system comprises a dichroic beam splitter and a filter, each being disposed between said optical source and said optical delivery structure.

14. A therapeutic radiation source according to claim 1, wherein said optical delivery structure is a fiber optic cable.

15. A therapeutic radiation source according to claim 1, wherein said probe assembly comprises an electrically conductive, flexible, outer sheath enclosing said optical delivery structure.

16. A therapeutic radiation source according to claim 1, wherein said photodetector comprises a photomultiplier tube.

17. A therapeutic radiation source according to claim 1, wherein said electrons incident on said target element from said electron source are accelerated by said electric field to energies in the approximate range of 10 keV to 90 keV.

18. A therapeutic radiation source according to claim 1, wherein the emitted electrons form an electron beam along a beam path, and wherein said target assembly is positioned in said beam path.

19. A therapeutic radiation source according to claim 18, wherein said electron beam is characterized by a current in the approximate range of 1 nA to 100 $\mu$A.

20. A therapeutic radiation source according to claim 1, wherein said scintillator is made of a crystalline material.

21. A therapeutic radiation source according to claim 20, wherein said crystalline material is selected from the group consisting of sodium-iodide, cesium-iodide, bismuth-germanate, cesium-fluoride, ZnS, YAP:Ce (yittrium aluminum perovskite), terbium doped glass fiber.

22. A therapeutic radiation source according to claim 1, wherein said scintillator is made of a material selected from the group consisting of glass, terbium doped glass fiber, and polymers.

23. A therapeutic radiation source-according to claim 1, wherein said electron source includes a photocathode having a photoemissive surface, said photocathode being positioned adjacent to said distal end of said optical delivery structure and being responsive to portions of said beam of optical radiation incident thereon from said distal end of said optical delivery structure to emit electrons from said photoemissive surface.

24. A therapeutic radiation source according to claim 1, wherein said electron source includes a thermionic cathode having an electron-emissive surface and adapted to emit electrons when heated to a sufficient temperature by a laser beam.

25. A therapeutic radiation source according to claim 1, wherein said radiation generator assembly further comprises a substantially rigid capsule enclosing said electron source and said target element and defining a substantially evacuated interior region extending along a beam axis, said capsule including a radiation transmissive window, wherein the therapeutic radiation emitted from said target element is directed through the radiation transmissive window.

26. A therapeutic radiation source according to claim 1, wherein said means for providing an accelerating voltage comprises a high voltage power supply.

27. A therapeutic radiation source according to claim 1, wherein said optical source is selected from the group consisting of a Nd:YAG laser, a diode laser, and a Nd:YVO4 laser.

28. A therapeutic radiation source according to claim 12, wherein said optical system includes Nd:YVO4 absorber material.

29. A therapeutic radiation source according to claim 1, wherein said optical source is a LED (light emitting diode).

30. A therapeutic radiation source, comprising:

A. a probe assembly including an optical delivery structure, said optical delivery structure having a proximal end and a distal end, and adapted for transmitting optical radiation incident on said proximal end to said distal end;

B. an optical source, including means for generating a beam of optical radiation directed to said proximal end of said optical delivery structure;

C. a radiation generator assembly coupled to said distal end of said optical delivery structure, the radiation generator assembly including:

a. an electron source, responsive to optical radiation transmitted to said distal end of said optical delivery structure, for emitting electrons to generate an electron beam along a beam path, the electron source including a thermionic cathode having an electron emissive surface; and b. a target element positioned in said beam path and spaced apart and opposite said electron emissive surface of said thermionic cathode, said target element including at least one radiation emissive material adapted to emit therapeutic radiation in response to incident accelerated electrons from said electron source;

wherein said optical delivery structure is adapted for directing a beam of said transmitted optical radiation to impinge upon said electron emissive surface of said thermionic cathode, said beam of optical radiation having a power level sufficient to heat at least a portion of said surface to an electron emitting temperature so as to cause thermionic emission of electrons from said surface;

D. means for providing an accelerating voltage between said electron source and said target element so as to establish an accelerating electric field which acts to accelerate electrons emitted from said electron source toward said target element; and E. an in situ radiation detecting system for monitoring an amount of the therapeutic radiation generated by said target element, said radiation detecting system including:

a. a scintillator disposed along a path of a portion of the therapeutic radiation emitted by said target element and adapted to generate scintillator light in response to the therapeutic radiation incident thereon, wherein the intensity of said scintillator light is proportional to the intensity of said incident therapeutic radiation;

b. a photodetector in optical communication with said scintillator by way of said optical delivery structure, for converting said scintillator light into a signal indicative of the intensity of the therapeutic radiation that is incident on said scintillator.

31. A therapeutic radiation source according to claim 30, wherein said electron emissive surface of said thermionic cathode is formed of a metallic material.

32. A therapeutic radiation source according to claim 31, wherein said metallic material comprises tungsten, thoriated tungsten, tungsten alloys, and tantalum.

33. A therapeutic radiation source according to claim 30, wherein the thermionic cathode comprises a metallic base coated with an oxide.

34. A therapeutic radiation source according to claim 33, wherein said oxide comprises barium oxide, strontium oxide, and calcium oxide, and said metallic base comprises nickel.

35. A therapeutic radiation source, comprising:

A. a probe assembly including a fiber optic cable having a proximal end and a distal end, said fiber optic cable being adapted for transmitting optical radiation incident on said proximal end to said distal end;

B. an optical source, including means for generating a beam of optical radiation directed to said proximal end of said optical delivery structure;

C. a radiation generator assembly coupled to the probe assembly, including:

a. an electron source, responsive to optical radiation transmitted to said distal end of said optical delivery structure, for emitting electrons to generate an electron beam along a beam path; and b. a target element positioned in said beam path, said target element including at least one radiation emissive material adapted to emit therapeutic radiation in response to incident electrons from said electron beam;

D. means for providing an accelerating voltage between said electron source and said target element so as to establish an accelerating electric field which acts to accelerate electrons emitted from said electron source toward said target element; and E. a photodetector in optical communication with said fiber optic cable;

wherein said fiber optic cable is formed of a scintillating material and disposed along a path of a portion of the therapeutic radiation emitted by said target element;

wherein said fiber optic cable being adapted to generate scintillator light in response to therapeutic radiation incident thereon, the intensity of said scintillator light being proportional to the intensity of said incident therapeutic radiation; and wherein said photodetector is adapted t o convert said scintillator light into a signal indicative of the intensity of said incident therapeutic radiation.

* * * * *